| United States Patent [19] | [11] | 4,310,635 |
|---|---|---|
| Hasegawa et al. | [45] | Jan. 12, 1982 |

[54] FERMENTATIVE PRODUCTION OF D(−)-β-HYDROXYISOBUTYRIC ACID

[75] Inventors: Junzo Hasegawa, Akashi; Masahiro Ogura, Ono; Shigeki Hamaguchi, Akashi; Masami Shimazaki, Takasago; Hajime Kawaharada, Kakogawa; Kiyoshi Watanabe, Akashi, all of Japan

[73] Assignee: Kanegafuchi Chemical Industry Co., Ltd., Osaka, Japan

[21] Appl. No.: 201,337

[22] Filed: Oct. 27, 1980

[30] Foreign Application Priority Data

Nov. 6, 1979 [JP] Japan .............................. 54-144252
Nov. 6, 1979 [JP] Japan .............................. 54-144253
Feb. 14, 1980 [JP] Japan .............................. 55-17559
Jul. 7, 1980 [JP] Japan .............................. 55-103805

[51] Int. Cl.³ .............................................. C12P 7/42
[52] U.S. Cl. .................................. 435/146; 435/911; 435/913; 435/917; 435/921; 435/938; 435/940; 435/942
[58] Field of Search ........................................ 435/146

[56] References Cited

U.S. PATENT DOCUMENTS 3,553,081  1/1971  Goodhue et al. ............... 435/146
4,211,846  7/1980  Lafferty ............................ 435/146

OTHER PUBLICATIONS

Methods in Enzymology, vol. 6, pp. 552–553 (1963).
Biochemische Zietschrift 1965, vol. 342, pp. 256–271.
Journal of Biological Chemistry, 1966, vol. 241, pp. 868–871.
Biotechnology and Bioengineering, 1971, vol. 13, pp. 203–214.

*Primary Examiner*—Lionel M. Shapiro
*Attorney, Agent, or Firm*—Armstrong, Nikaido, Marmelstein & Kubovcik

[57] ABSTRACT

A process is disclosed wherein D(−)-β-hydroxyisobutyric acid is produced fermentatively from isobutyric acid or methacrylic acid by the stereoselective action of microorganisms having the ability to convert isobutyric acid or methacrylic acid into D(−)-β-hydroxyisobutyric acid in an aqueous medium, and D(−)-β-hydroxyisobutyric acid is recovered from the aqueous medium.

13 Claims, No Drawings

FERMENTATIVE PRODUCTION OF D(−)-β-HYDROXYISOBUTYRIC ACID

BRIEF SUMMARY OF THE INVENTION

The present invention relates to a process for production of D(−)-β-hydroxyisobutyric acid (hereinafter referred to as D-HIBA). More specifically, the present invention relates to a process for advantageous production of D-HIBA utilizing the special ability of microorganisms to produce optically active compound by asymmetric synthesis.

D-HIBA is one of useful intermediates for synthesis of physiologically active substances having asymmetric carbon atoms such as medicines exemplified by 1-(D-3-mercapto-2-methyl propanoyl)-L-proline, an antihypertensive.

As methods for production of β-hydroxyisobutyric acid (hereinafter referred to as HIBA), chemical synthesis from formaldehyde and ethyl α-bromopropionate by the Reformatsky reaction, for example, is known (E. E. Blaise and I. Herman: Ann. Chim. et phys. 17, 371, 1969); however, HIBA obtained by this method is the optically inactive DL(±)form. This method is therefore disadvantageous for production of optically active HIBA in that complicated processes of chemical resolution, in which an expensive reagent such as quinine is used, are further required for obtaining it (J. Retey and F. Lynen: Biochemische Zeitschrift, 342, 256–271, 1965). A method for obtaining D-HIBA by chemical synthesis without optical resolution was reported by M. Sprecher and D. B. Sprinson (Journal of Biological chemistry, 241, 868, 1966); however, the starting material in this method, threo-3-methyl-L-aspartic acid, is very expensive and the synthetic procedures are exceedingly complicated. On the other hand, a method for production of optically active HIBA by fermentation employing Pseudomonas putide (Charles T. Geodhue and James R. Schaeffer: Biotechnology and Bioengineering 13, 203, 1971) was presented; however, HIBA produced by this method is the L(+) form.

Thus there has not been any industrially advantageous process for production of D-HIBA. The present inventors noticed that microbial processes which utilize stereospecific catalysis characteristic of microorganisms have often been demonstrated to be more advantageous for production of optically active compounds than chemical resolution of racemic compounds. The present inventors have now found that there are microorganisms which have the ability to convert isobutyric acid (hereinafter referred to as IBA) or methacrylic acid (hereinafter referred to as MA) into D-HIBA. Based on his finding, the present inventors have completed the present invention which is a fermentative method for production of D-HIBA from IBA, MA, or a mixture of IBA and MA.

In the present invention, a substrate selected from the group consisting of IBA, MA, and a mixture thereof, which is readily available at a low price and in large quantities, is subjected to the action of a microorganism having the ability to convert the substrate into D-HIBA. Conversion of the substrate into D-HIBA by catalysis of the microorganism is carried out in two ways. In one way, the microorganism is cultivated aerobically in an aqueous nutrient medium containing the substrate, whereby propagation of the microorganism and subjection of the substrate to the action of the microorganism are carried out simultaneously in one step. In the other way, the microorganism is first cultivated in an aqueous nutrient medium, then the substrate is added to the resulting culture broth or to the suspension of cells obtained in the first step, and subsequently the mixture is incubated aerobically. Microorganisms employed in the present invention convert the substrate into only the D(−)form of HIBA in high yield; therefore, according to the present invention, D-HIBA can be produced by a simple process at a low cost.

DETAILED DESCRIPTION

Microorganisms employed in the present invention have the ability to convert IBA or MA into D-HIBA and can easily be selected from type cultures or strains isolated from nature by the following procedures:

IBA or MA is added, in an amount attaining a concentration of about 2% w/v, to a culture broth obtained by cultivating a microbial strain in a nutrient medium in which the test strain can grow. The resulting culture broth, adjusted to pH 6–9, is incubated aerobically at 25°–35° C. for 1–3 days. After incubation, a highly water-soluble salt such as ammonium sulfate and sodium sulfate is added to the culture broth and pH is lowered to below 2 in order to facilitate extraction of D-HIBA from the culture broth. The culture broth is extracted with a water-immiscible solvent such as ethyl acetate. The solvent layer is evaporated and dried over anhydrous sodium sulfate, and then the optical rotation of the extract measured in a methanol solution. Extract samples exhibiting levorotation are selected and applied onto a silica gel thin layer plate. If a sample shows the same mobility as that of HIBA, the microorganism employed for preparing the sample almost always has the ability to convert IBA or MA into D-HIBA. In order to confirm production of D-HIBA, the extract sample is further purified by column chromatography over silica gel and the structure of the purified preparation is determined by instrumental analysis such as NMR, IR, and so forth. In view of results obtained in this screening of D-HIBA-producing microorganisms, most of culture broth of which a solvent extract exhibits levorotation contain D-HIBA. Therefore, this screening method is simple and makes it very easy to find out microorganisms capable of producing D-HIBA from IBA or MA.

All D-HIBA-producing microorganisms selected by the foregoing screening method can be employed in the present invention; for example, microorganisms belonging to the following genera are employed: Candida, Torulopsis, Trygonopsis, Saccharomyces, Pichia, Debaryomyces, Wingea, Rhodosporidium, Aspergillus, Choanephora, and Zygorhynchus.

Among microorganisms belonging to the genera illustrated above, the following strains, for example, are employed in the present invention:

*Candida rugosa* IFO 0750, *Candida rugosa* IFO 0591, *Candida parapsilosis* IFO 0708, *Candida utilis* IFO 0396, *Torulopsis candida* IFO 0380, *Trygonopsis variabilis* IFO 0671, *Saccharomyces cerevisiae* IAM 4274, *Saccharomyces rouxii* IFO 0493, *Pichia membranaefaciens* IAM 4904, *Debaryomyces hansenii* IFO 0026, *Wingea robertsii* IFO 1277, *Rhodosporidium toruloides* IFO 0559, *Aspergillus niger* IAM 2532, *Choanephora circinanus* HUT 1324, and *Zygorhynchus moelleri* HUT 1305.

Note:
  IFO: Institute for Fermentation, Osaka; Juso Nishinomachi, Higashi-yodogawa-ku, Osaka, Japan IAM: Institute of Applied Microbiology, University of Tokyo; 1-chrome, Yayoi, Bunkyo-ku, Tokyo, Japan HUT: Faculty of Engineering, Hiroshima University; 3-chrome, Senda-machi, Hiroshima City, Japan For subjecting the substrate to the action of the microorganism, two ways are available. In one way, the microorganism is cultivated aerobically in an aqueous medium containing the substrate from the beginning of the cultivation, thereby D-HIBA accumulating in the medium simultaneously with propagation of the microorganism. In the other way, the process consists of two steps, that is, cultivation of the microorganism and subjection of the substrate to the action of the microorganism. The first step of the two-step process can be carried out by cultivating the microorganism in an aqueous nutrient medium. The second step of the two-step process can be carried out by adding the substrate to a culture broth obtained in the first step or a suspension of cells obtained in the first step followed by incubating the resulting mixture aerobically. The suspension of cells is prepared by separating cells from a culture broth of the microorganism by centrifugation, and so forth followed by suspending the cells in an appropriate aqueous medium such as an aqueous phosphate buffer solution. Since enzymes of microorganisms are involved in the reaction of the process of the present invention, the separated cells can also be subjected to various treatments, such as drying and homogenization, etc., before suspension in the medium in order to promote the enzyme reaction. Therefore, use of cells treated in various ways should be construed as being covered by the scope of the present invention.

For cultivation of the microorganism, any medium in which the microorganism employed is able to grow can be used. The medium usually contains a carbon source, a nitrogen source, and if necessary a mineral source, and so forth. Examples of carbon sources in the medium include carbohydrates such as glucose, sucrose, starch, hydrolysates, and molasses; organic acids such as acetic acid, fumaric acid, and lactic acid; alcohols such as methanol, ethanol, and propanol; and further liquid hydrocarbons such as n-paraffins and olefines, oils and fats, glycerol, and so forth, which can be assimilated by the employed microorganisms. As a nitrogen source in the medium, inorganic or organic compounds such as ammonium sulfate, ammonium chloride, ammonium phosphate, ammonia water, urea, amino acids, peptone, and hydrolysates of soy bean protein are used. As a mineral in the medium, inorganic acid salts of potassium, magnesium, zinc, iron, manganese, copper, or calcium can be used. If necessary, yeast extract, meat extract, corn steep liquor, vitamins, or nucleic acid-related substances such as adenine and guanine may be added to the medium.

As to cultivating conditions, there is not any particular difference between the foregoing two methods. Cultivation of the microorganism can be carried out under any conditions which allow the microorganism to grow, but preferably at a pH of from about 4.0 to about 9.5 and a temperature of from about 20° C. to about 40° C. In the foregoing two-step process, it is effective in promoting the reaction in the second step to induce those enzymes of the microorganism, which catalyze the conversion of the substrate into D-HIBA, by addition of a small amount of the substrate to the medium in the first step. Incubation of the second step in the foregoing two-step process can be carried out, preferably, at a pH of from about 6.0 to about 9.5 and a temperature of from about 20° C. to about 40° C.

For isolation of D-HIBA from the culture broth or reaction mixture, usual methods for extraction and purification of an organic acid, such as solvent extraction and ion exchange, can be employed. An example of an efficient recovering method by solvent extraction is shown as follows: The culture broth or reaction mixture is acidified with a mineral acid such as sulfuric and hydrochloric acids, an inorganic salt such as ammonium sulfate and sodium sulfate added thereto if necessary to increase the ionic strength of the broth or mixture, and extracted with a water-immiscible solvent such as butanol, methyl-isobutyl ketone, and ethyl acetate. Crude D-HIBA is obtained by evaporation of the solvent layer to dryness. The D-HIBA preparation thus obtained can further be purified by column chromatography using silica gel, etc. to give D-HIBA of high purity.

The following examples will illustrate the present invention in greater detail.

EXAMPLE 1

Candida rugosa IFO 0750, Candida rugosa IFO 0591, Candida parapsilosis IFO 0708, Candida utilis IFO 0396, Torulopsis candida IFO 0380, Trygonopsis variabilis IFO 0671, Saccharomyces cerevisiae IAM 4274, Saccharomyces rouxii IFO 0493, Pichia membranaefaciens IAM 4904, Debaryomyces hansenii IFO 0026, Wingea robertsii IFO 1277, Rhodosporidium toruloides IFO 0559, Aspergillus niger IAM 2532, Choanephora circinanus HUT 1324, and Zygorhynchus moelleri HUT 1305 were each inoculated in a medium comprising 40 g glucose, 5 g yeast extract, 3 g peptone, 1 g meat extract; and 20 g IBA, or 20 g MA, or a 20 g mixture consisting of equal amounts (weight) of IBA and MA. The microorganisms were each cultivated in a 3-L jar fermentor at 30° C., pH 7.5 agitation 500 rpm, and aeration 1 vv for 24 hr. Then, pH was elevated to 8.5 and the cultivation was continued for further 48 hr. The culture broth thus obtained was acidified with sulfuric acid to give pH 2.0, saturated with ammonium sulfate, and extracted with ethyl acetate in an amount equal by volume to that of the culture broth. The extract, dried over anhydrous sodium sulfate, was concentrated under reduced pressure. The concentrated oily substance, dissolved in a small amount of benzene, was applied onto a column packed with silica gel. The elution was carried out at first with benzene-acetone (9:1 by volume) to remove unchanged IBA or MA, and then with benzene-acetone (3:1 by volume) to elute D-HIBA. Fractions containing D-HIBA were combined and concentrated under reduced pressure to give a viscous liquid. The liquid thus obtained was identified as HIBA by gas chromatography, silica gel TLC (Thin-layer chromatography), NMR spectrum, etc. The optical rotation of each product was measured to give the result of $[\alpha]_D^{25}$ 13°–18° (C=3, methanol), which demonstrates that HIBA thus produced by each microorganism is the D(—)-form. Yields of D-HIBA prepared by the method described above are shown in Table 1.

TABLE 1

| Microorganism | Yield of D-HIBA (g) Substrate | | |
|---|---|---|---|
| | IBA | MA | IBA + MA |
| Candida rugosa IFO 0750 | 8.2 | 7.9 | 7.8 |
| Candida rugosa IFO 0591 | 6.5 | 7.8 | 8.4 |
| Candida parapsilosis IFO 0708 | 5.5 | 6.2 | 5.5 |
| Candida utilis IFO 0396 | 5.4 | 8.8 | 5.3 |

TABLE 1-continued

| Microorganism | Yield of D-HIBA (g) Substrate | | |
|---|---|---|---|
| | IBA | MA | IBA + MA |
| Torulopsis candida IFO 0380 | 2.1 | 1.1 | 3.6 |
| Trygonopsis variabilis IFO 0671 | 5.8 | 2.5 | 2.9 |
| Saccharomyces cerevisiae IAM 4274 | 3.2 | 1.7 | 3.3 |
| Saccharomyces rouxii IFO 0493 | 4.6 | 2.0 | 4.0 |
| Pichia membranaefaciens IAM 4904 | 7.0 | 1.3 | 1.9 |
| Debaryomyces hansenii IFO 0026 | 9.2 | 4.3 | 7.0 |
| Wingea robertsii IFO 1277 | 1.9 | 0.8 | 1.1 |
| Rhodosporidium toruloides IFO 0559 | 2.5 | 4.0 | 2.2 |
| Aspergillus niger IAM 2532 | 2.3 | 2.3 | 3.5 |
| Choanephora circinanus HUT 1324 | 1.8 | 1.5 | 0.6 |
| Zygorhynchus moelleri HUT 1305 | 1.3 | 1.1 | 1.5 |

EXAMPLE 2

The same strains as used in Example 1 were each inoculated in 1 L of a medium comprising 20 g glucose, 5 g yeast extract; 1 g IBA or 1 g MA, or a 1 g mixture consisting of equal amounts (weight) of IBA and MA. The microorganisms were each cultivated in a 3-L jar fermentor at 30° C., pH 6.0, agitation 500 rpm, and aeration 1 vvm for 20 hr. Then, 30 g of IBA, MA, or a 30 g mixture consisting of equal amounts (weight) of IBA and MA was added to the resulting culture broth. The culture broth, adjusted to pH 8.5, was incubated for 72 hr. After incubation, the reaction mixture was treated in the same manner as described in Example 1 to give D-HIBA. The range of the optical rotation of D-HIBA thus obtained was the same as that in Example 1. Yields of D-HIBA are shown in Table 2.

TABLE 2

| Microorganism | Yield of D-HIBA (g) Substrate | | |
|---|---|---|---|
| | IBA | MA | IBA + MA |
| Candida rugosa IFO 0750 | 8.3 | 10.2 | 7.8 |
| Candida rugosa IFO 0591 | 6.1 | 9.4 | 8.5 |
| Candida parapsilosis IFO 0708 | 7.7 | 10.5 | 9.7 |
| Candida utilis IFO 0396 | 5.7 | 6.1 | 4.7 |
| Torulopsis candida IFO 0380 | 1.9 | 1.6 | 3.3 |
| Trygonopsis variabilis IFO 0671 | 5.0 | 4.3 | 3.6 |
| Saccharomyces cerevisiae IAM 4274 | 3.2 | 1.5 | 3.8 |
| Saccharomyces rouxii IFO 0493 | 4.4 | 1.8 | 2.0 |
| Pichia membranaefaciens IAM 4904 | 4.5 | 1.7 | 1.8 |
| Debaryomyces hansenii IFO 0026 | 8.5 | 5.9 | 8.6 |
| Wingea robertsii IFO 1277 | 2.2 | 0.6 | 3.1 |
| Rhodosporidium toruloides IFO 0559 | 2.4 | 0.8 | 2.5 |
| Aspergillus niger IAM 2532 | 2.3 | 1.0 | 1.2 |
| Choanephora circinanus HUT 1324 | 0.9 | 0.7 | 0.5 |
| Zygorhynchus moelleri HUT 1305 | 1.8 | 0.9 | 2.2 |

EXAMPLE 3

The same strains as used in Example 1 were each inoculated in 1 L of a medium comprising 20 g glucose, 5 g yeast extract, 3 g peptone, 3 g meat extract; 1 g IBA or 1 g MA, or a 1 g mixture consisting of equal amounts (weight) of IBA and MA. The microorganisms were each cultivated in a 3-L jar fermentor at 30° C., pH 6.0, agitation 500 rpm, and aeration 1 vvm for 24 hr. Cells were harvested by centrifugation from the culture broth thus obtained, washed twice with a 0.9% saline solution, and suspended in 1/15 M phosphate buffer (pH 8.5). To the cell suspension were added 30 g of IBA, MA, or a 30 g mixture of IBA and MA (IBA:MA = 1:1 by weight), and 30 g glucose. The resulting mixture was incubated at pH 8.5 for 48 hr. After incubation, the reaction mixture was treated in the same manner as described in Example 1 to give D-HIBA. The range of the optical rotation of D-HIBA thus obtained was the same as that in Example 1. Yields of D-HIBA are shown in Table 3.

TABLE 3

| Microorganism | Yield of D-HIBA (g) Substrate | | |
|---|---|---|---|
| | IBA | MA | IBA + MA |
| Candida rugosa IFO 0750 | 9.4 | 9.2 | 8.8 |
| Candida rugosa IFO 0591 | 8.3 | 7.7 | 9.5 |
| Candida parapsilosis IFO 0708 | 11.0 | 9.9 | 9.3 |
| Candida utilis IFO 0396 | 6.2 | 5.9 | 4.4 |
| Torulopsis candida IFO 0380 | 2.1 | 1.5 | 2.0 |
| Trygonopsis variabilis IFO 0671 | 4.4 | 5.0 | 4.6 |
| Saccharomyces cerevisiae IAM 4274 | 2.5 | 2.1 | 1.8 |
| Saccharomyces rouxii IFO 0493 | 3.6 | 3.3 | 4.2 |
| Pichia membranaefaciens IAM 4904 | 7.4 | 8.5 | 8.8 |
| Debaryomyces hansenii IFO 0026 | 6.2 | 4.7 | 5.1 |
| Wingea robertsii IFO 1277 | 1.5 | 1.6 | 1.3 |
| Rhodosporidium toruloides IFO 0559 | 2.0 | 1.5 | 1.7 |
| Aspergillus niger IAM 2532 | 0.7 | 1.2 | 1.4 |
| Choanephora circinanus HUT 1324 | 1.1 | 1.8 | 2.2 |
| Zygorhynchus moelleri HUT 1305 | 1.6 | 2.2 | 1.6 |

What is claimed is:

1. A process for producing D(—)-$\beta$-hydroxyisobutyric acid which comprises subjecting a substrate selected from the group consisting of isobutyric acid, methacrylic acid, and a mixture of isobutyric acid and methacrylic acid to the action of a microorganism having the ability to convert the substrate into D(—)-$\beta$-hydroxyisobutyric acid in an aqueous medium and recovering D(—)-$\beta$-hydroxyisobutyric acid from the medium.

2. The process according to claim 1 wherein said microorganism belongs to a genus selected from the group consisting of the genus Candida, Torulopsis, Trygonopsis, Saccharomyces, Pichia, Debaryomyces, Wingea, Rhodosporidium, Aspergillus, Choanephora, and Zygorhynchus.

3. The process according to claim 1 wherein said microorganism belongs to a species selected from the group consisting of *Candida rugosa, Candida parapsilosis, Candida utilis, Torulopsis candida, Trygonopsis variabilis, Saccharomyces cerevisiae, Saccharomyces rouxii, Pichia membranaefaciens, Debaryomyces hansenii, Wingea robertsii, Rhodosporidium toruloides, Aspergillus niger, Choanephora circinanus, and Zygorhynchus moelleri.*

4. The process according to claim 1, claim 2, or claim 3 wherein the microorganism is cultivated aerobically in an aqueous medium containing the substrate.

5. The process according to claim 4 wherein the cultivation is carried out at a pH of from about 4 to about 9.5 and a temperature of from about 20° C. to about 40° C.

6. The process according to claim 1, claim 2, or claim 3 wherein the substrate is added to a culture broth obtained by cultivating the microorganism in an aqueous medium and then the resulting mixture is incubated aerobically.

7. The process according to claim 6 wherein a small amount of isobutyric acid, methacrylic acid, or a mixture of isobutyric acid and methacrylic acid is added in the aqueous medium when the microorganism is cultivated to induce enzymes of the microorganism.

8. The process according to claim 6 wherein the microorganism is cultivated at a pH of from about 4.0 to about 9.5 and a temperature of from about 20° C. to about 40° C. and the mixture is incubated at a pH of from about 6.0 to about 9.5 and a temperature of from about 20° C. to about 40° C.

9. The process according to claim 1, claim 2, or claim 3 wherein the substrate is added to a cell suspension prepared by separating cells from a culture broth obtained by cultivating the microorganism in an aqueous medium followed by suspending the cells in an aqueous medium and then the resulting mixture is incubated aerobically.

10. The process according to claim 9 wherein a small amount of isobutyric acid, methacrylic acid, or a mixture of isobutyric acid and methacrylic acid is added in the aqueous medium when the microorganism is cultivated to induce enzymes of the microorganism.

11. The process according to claim 9 wherein the microorganism is cultivated at a pH of from about 4.0 to about 9.5 and a temperature of from about 20° C. to about 40° C. and the mixture is incubated at a pH of from about 6.0 to about 9.5 and a temperature of from about 20° C. to about 40° C.

12. The process according to claim 1, claim 2, or claim 3 wherein D(−)-$\beta$-hydroxyisobutyric acid is recovered from the aqueous medium by extraction with a water-immiscible solvent.

13. The process according to claim 12 wherein the water-immiscible solvent is butanol, methyl-isobutyl ketone, or ethyl acetate.

* * * * *